United States Patent [19]

Leach

[11] 4,060,560
[45] Nov. 29, 1977

[54] DISPROPORTIONATION OF XYLENOLS WITH PHENOL TO FORM CRESOLS

[75] Inventor: Bruce Eugene Leach, Ponca City, Okla.

[73] Assignee: Continental Oil Company, Ponca City, Okla.

[21] Appl. No.: 670,772

[22] Filed: Mar. 26, 1976

[51] Int. Cl.² ............................................. C07C 39/04
[52] U.S. Cl. ........................ 260/621 D; 260/621 E; 260/624 E
[58] Field of Search ........... 260/621 E, 621 D, 621 R, 260/624 R, 624 C, 624 E

[56] References Cited

U.S. PATENT DOCUMENTS

| | | | |
|---|---|---|---|
| 2,295,675 | 9/1942 | Meharg et al. | 260/621 D |
| 3,417,149 | 12/1968 | Neworth et al. | 260/621 D |
| 3,446,856 | 5/1969 | Hamilton | 260/620 R |
| 3,479,410 | 11/1969 | Hamilton | 260/621 R |
| 3,998,892 | 12/1976 | Leach | 260/621 D |

FOREIGN PATENT DOCUMENTS

| | | | |
|---|---|---|---|
| 45-39525 | 12/1970 | Japan | 260/621 E |
| 1,291,191 | 10/1972 | United Kingdom | 260/621 D |
| 1,232,027 | 5/1971 | United Kingdom | 260/621 D |

OTHER PUBLICATIONS

Jelineh, "Chem. Abstracts", vol. 55, 7357 (1961).

*Primary Examiner*—James O. Thomas, Jr.
*Assistant Examiner*—W. B. Lone
*Attorney, Agent, or Firm*—Cortlan R. Schupbach, Jr.

[57] ABSTRACT

Xylenols are disproportionated with phenol over catalysts such as tungsten oxide promoted magnesium oxide, preferably in the presence of water. The reaction selectively removes methyl groups ortho to the hydroxyl group. Catalysts which can be used are magnesium oxide promoted with zinc oxide, tungsten oxide, and uranium oxide.

8 Claims, No Drawings

DISPROPORTIONATION OF XYLENOLS WITH PHENOL TO FORM CRESOLS

This invention relates to a method for disproportionating xylenols with phenol. More particularly, this invention relates to a method for disproportionating xylenols with phenol over magnesium oxide catalyst promoted with compounds such as tungsten oxide, zinc oxide, and uranium oxide to form cresols.

Meta,para-cresols have been previously synthesized by methylation of phenol using high acidity catalysts such as aluminas or silicas, phosphoric acid on kielseger and the like. Another method has been the isomerization of orthocresol by similar catalysts of high acidity. Examples of such processes are U.S. Pat. No. 3,417,149 which carries out a proportionation reaction using alumina catalysts with or without silicas. British Pat. No. 1,291,191 also teaches liquid phase disproportionation in the presence of catalysts such as aluminum phenolate, methylate, or oxide. U.S. Pat. No. 3,479,410 discloses vapor phase methylation of phenols over magnesium oxide by passing said phenols over the catalyst in the presence of 2,4,6-trimethylphenol. 2,4,6-trimethylphenol is necessary as an ingredient in the feed stream. The patent relates to vapor phase methylation of phenols having at least one ortho hydrogen.

Magnesium oxide which is specifically shaped by bonding with an inert, organic polymeric binder as described in U.S. Pat. No. 3,843,606 is used for the ortho-alkylation of phenols. The use of the inert organic binder is taught to be beneficial in extending catalyst life. This, while an advance, leaves one with the problem of regeneration of the magnesium oxide. Such regeneration is normally carried out by combustion of carbon with air in steam or other atmosphere to control the rate of combustion, achieving temperatures of about 500° C. Using the inert, organic polymeric binder described in this patent, however, such regeneration is not possible once the catalyst is deactivated. Such a polymeric binder interfers with the high temperature regeneration and thus the catalyst must be disposed when activity ceases. A catalyst which is not bonded to such a polymer but rather to silica-type binders, can be regenerated many times; thus it can be seen that the organic polymeric binder, which is in itself expensive and which requires an extra operation on the catalyst before use, is ineffective and inefficient under conditions of extensive use.

Another catalyst is taught in U.S. Pat. No. 3,873,628 wherein manganese sulfate is mixed with magnesium oxide. The resulting catalyst is an ortho director when an alkyl alcohol is reacted with a phenolic compound. The combination is said to allow the alkylation to proceed at a lower temperature without reducing selectivity to the ortho position. However, the reaction produces sulfur dioxide as a by-product and must be removed before disposal in the atmosphere.

These patents without exception teach the alkylation of phenols. However, in many instances the desired product will be a cresol and the starting material available will be a dialkylated phenol. Thus, alkylation in the ortho position is not desired in the instant invention but rather a dealkylation is desired in order to produce meta,para-cresol and ortho cresols. Meta,para-cresol as used herein designates mixtures of m-cresol and p-cresol.

It would be very desirable to use a catalyst without the high acidity of those previously used. Magnesium oxide catalysts previously used in such reactions, while of low acidity, have required the incorporation of compounds such as 2,4,6-trimethylphenol in order to carry out the reaction or alternatively utilize particular substrates for the catalyst, such as an inert organic cellulosic polymeric binder described in U.S. Pat. No. 3,843,606. It would be of great benefit to be able to carry out the reaction in the absence of such compounds. In addition, it would be greatly desirable to find an additional use for xylenol fractions.

It is therefore an object of the present invention to provide a process to selectively synthesize cresols having methyl groups in the meta and para positions. Other objects will become apparent to those skilled in this art as the description proceeds.

It has now been found in accordance with the present invention that xylenols can be selectively converted to cresols in the presence of phenol over magnesium oxide-based catalysts in vapor phase reactions. The reactions are carried out generally at temperatures between 340° and 550° C. The magnesium oxide catalysts used are promoted with tungsten oxide, zinc oxide, uranium oxide, or mixtures of these to increase reaction rates and selectivity. Of these, tungsten oxide is the preferred promoter. Trimethylphenols and pentamethylphenols can be included in the feed stream but are not necessary for the reaction to be efficient. In addition, water in the feed in the amounts of 5 to 15 weight percent has been found to be beneficial to the reaction.

Tungsten is known as an olefin disproportionation promoter, as disclosed in U.S. Pat. No. 3,865,751, and as a vanadium oxide catalyst promoter as taught in U.S. Pat. No. 3,855,318. The prior art has not heretofore appreciated the vastly increased catalyst life and improved reaction rates obtainable when magnesium oxide and tungsten oxide are used together.

The xylenols used as a feed stream in the process of the instant invention can be 2,3-xylenol, 2,4-xylenol, 2,5-xylenol, and 2,6-xylenol, or mixtures of these. Various xylenol-starting materials can shift the product distribution of the cresols obtained. For example, any 2,6-xylenol in the feed stream will yield predominantly ortho-cresol, 2,3/2,5 xylenols in the feed stream will yield predominantly meta-cresol, while 2,4-xylenol yields predominantly para-cresol and ortho-cresol. The feed stream will largely determine the cresols obtained as products, but the catalysts of the instant invention provide additional selectivity in addition to increased reaction rates.

The reaction may be carried out in either a batch or a continuous reactor, but a continuous reactor is preferred. When carried out in a continuous reactor, a liquid hourly space velocity (LHSV) of 0.1 to 5.0 is used, and from about 0.5 to about 2.0 is preferred. While no significant benefit has been found in using pressures above atmospheric, up to 1,000 pounds per square inch gauge (psig) can be used.

The catalysts of the instant invention are not found to deactivate as rapidly as the prior art catalysts under the conditions of the instant invention. The catalyst promoters are added, depending upon the reaction and feed stream, in amounts of from about 0.5 to 15 percent of the total catalyst weight used. When the catalyst is used in a fluid bed operation, the amount used is that sufficient to effect the reaction at the LHSV used.

While deactivation does occur, catalyst lifetime is found to be in the range of about 100 hours. While zinc oxide and uranium oxide promoters regenerate in a satisfactory manner, subsequent reactions carried out using these catalysts show progressively decreased activity and shorter lifetimes with successive regenerations.

Tungsten oxide promoted catalysts surprisingly are not adversely affected, and indeed improve in activity over the original fresh catalyst after a short induction period which is apparent directly after regeneration. Catalyst life is likewise not decreased by regeneration, being in the range of about 100 hours. These results are surprising in view of the location of tungsten in the Periodic Table, the fact that tungsten oxide alone will not catalyze the reaction, and the failure of other regenerated catalysts to regain full activity. These properties of tungsten are shown in Example 6.

Regeneration of the catalyst can be carried out by first cleaning the reactor containing the deactivated catalyst with steam. Air mixed with steam is introduced into the reactor. The amount of air is controlled to maintain temperature in the reactor at about 500° C. Air content is gradually increased until no exotherm is observed. The reactor is then purged with steam or an inert gas before restarting the reaction.

The catalysts of the instant invention can be prepared by means well known to those skilled in this art. Concisely, the procedure is as follows; magnesium oxide is mixed with about 2 percent by weight of silica or sodium silicate or other suitable inert binder and the desired amount of promoter. The mixture is pelletized, and the resulting pellets heated to about 450° C. The promoters can be added as oxides or acid forms. For example, tungsten can be added as $WO_3$ or $H_2WO_4$ (tungstic acid). Pellets are preferred in a continuous reactor to insure adequate reactant flow.

The invention is more concretely described with reference to the examples below wherein all parts and percentages are by weight unless otherwise specified. The examples are intended to exemplify the present invention and should not be construed to limit it. Examples 1 and 2 directly compare unpromoted magnesium oxide to promoted magnesium oxide.

EXAMPLE 1

A reaction was carried out in a ⅜ inch stainless steel reactor containing approximately 15 cubic centimeters (cc) of catalyst. The catalyst used was magnesium oxide with no promoter (Merck Maglite D, ⅛ inch diameter pellets). A feed mixture consisting of, by weight, 40 parts phenol, 54 parts 2,6-xylenol, 6 parts mixed cresols, and 10 parts water were passed through the reactor at a liquid hourly space velocity (LHSV) of 1.0. The reaction was carried out at three temperatures, with the results shown in weight percent.

|  | REACTION PRODUCTS | | |
|---|---|---|---|
|  | 450° C | 475° C | 500° C |
| phenol | 34.9 | 30.7 | 28.0 |
| o-cresol | 7.0 | 18.3 | 24.1 |
| 2,6-xylenol | 48.6 | 38.3 | 34.0 |

EXAMPLE 2

A reaction was carried out using the same feed and conditions as described above. To the catalyst was added 3 weight percent $H_2WO_4$. The reaction products are shown in weight percent for temperatures of 450° and 460° C.

|  | 450° C | 460° C |
|---|---|---|
| phenol | 30.8 | 28.2 |
| o-cresol | 25.1 | 30.0 |
| 2,6-xylenol | 25.3 | 18.0 |

A comparison of the 450° C results shows that the promoted magnesium oxide produces nearly four times as much of the desired o-cresol as unpromoted magnesium oxide.

EXAMPLE 3

The reaction was carried out in the same manner as described for Example 1. A feed of 60 parts of 2,6-xylenol, 40 parts phenol, and 10 parts of water was passed through the reactor at 500° C and a LHSV of 2.0. The catalyst used was magnesium oxide mixed with 5 percent by weight, based on the total weight of the catalyst, of uranium oxide. The products were again analyzed using gas chromatography. Product distribution was:

| Products: | wt % |
|---|---|
| phenol | 26.1 |
| o-cresol | 28.9 |
| m,p-cresol | 6.3 |
| 2,6-xylenol | 29.3 |
| 2,4-xylenol | 6.5 |
| 2,3-xylenol | 0.3 |
| 2,4,6-xylenol | 2.5 |

EXAMPLE 4

Example 4 was carried out exactly as described above except zinc oxide catalyst was used in place of the catalyst of Example 3. The product distribution changed as shown below:

| Product: | wt % |
|---|---|
| phenol | 34.4 |
| o-cresol | 23.0 |
| m,p-cresol | 4.7 |
| 2,6-xylenol | 35.7 |
| 2,4/2,5-xylenol | 1.6 |
| 2,3-xylenol | 0.2 |
| 2,4,6-trimethylphenol | 0.1 |
| High Boilers | 0.1 |

EXAMPLE 5

Ten weight percent tungsten oxide dissolved in dilute ammonium hydroxide was placed on formed magnesium oxide. The reaction was then carried out as described above at a temperature of 450° C and an LHSV of 1.5 using the same feed described in Example 3. The following product distribution was observed:

| Product | wt % |
|---|---|
| phenol | 29.0 |
| o-cresol | 25.5 |
| m,p-cresol | 5.6 |
| 2,6-xylenol | 32.4 |
| 2,4/2,5-xylenol | 4.6 |
| 2,4,6-trimethylphenol | 2.7 |

During the course of the reaction, conversion to ortho-cresol remained above 20 percent for 30 hours at a temperature of 450° C. Slow catalyst deactivation was noticed. Catalyst life is about 100 hours. Catalyst regeneration was successful.

EXAMPLE 6

The use and regeneration of a $WO_3/MgO$ catalyst was studied using a feed of 51.3 parts 2,6-xylenol, 5.7 parts of a mixture of m,p-cresol, 43 parts phenol, and 10 parts water. The reactor volume contained ⅔ inert ceramic saddles and ⅓ pelletized catalyst. A space velocity of 0.33 LHSV was used, and the temperature was gradually increased throughout the reaction. The results of carrying out the reaction using fresh catalyst are shown in Table A, after the first regeneration in Table B, after a second regeneration in Table C, and and after a third regeneration in Table D.

TABLE A

| Temp. ° C | 465 | 475 | 485 | 485 | 495 |
|---|---|---|---|---|---|
| Reaction Hours | 10 | 35 | 60 | 65 | 85 |
| Cumulative Hours Total | 10 | 35 | 60 | 65 | 85 |
| Product Composition (dry basis) weight % | | | | | |
| phenol | 31.3 | 33.2 | 31.9 | 32.2 | 33.3 |
| o-cresol | 24.5 | 21.7 | 21.1 | 22.2 | 19.0 |
| m,p-cresol | 5.7 | 5.3 | 5.3 | 5.3 | 5.2 |
| 2,6-xylenol | 32.4 | 36.0 | 37.4 | 35.9 | 39.1 |
| 2,4/2,5-xylenol | 4.1 | 2.6 | 2.7 | 2.8 | 2.3 |
| 2,3/3,5-xylenol | 0.1 | 0.1 | 0.1 | 0.2 | 0.1 |
| 2,4,6-trimethylphenol | 1.9 | 1.3 | 1.3 | 1.4 | 1.0 |

TABLE B

| Temp. ° C. | 460 | 460 | 460 | 470 | 470 |
|---|---|---|---|---|---|
| Reaction Hours | 0.5 | 2.5 | 20 | 24 | 44 |
| Cumulative Hours Total | 85.5 | 87.5 | 105 | 109 | 129 |
| Product Composition (dry basis) weight % | | | | | |
| phenol | 35.9 | 31.3 | 31.6 | 30.9 | 31.3 |
| o-cresol | 15.7 | 22.2 | 21.4 | 26.0 | 23.1 |
| m,p-cresol | 6.0 | 7.9 | 5.9 | 5.6 | 5.5 |
| 2,6-xylenol | 36.5 | 29.0 | 34.5 | 31.0 | 34.2 |
| 2,4/2,5-xylenol | 2.6 | 6.3 | 4.4 | 4.5 | 3.8 |
| 2,3/3,5-xylenol | 0.1 | 0.1 | 0.2 | 0.1 | 0.2 |
| 2,4,6-trimethylphenol | 3.2 | 2.9 | 1.7 | 1.8 | 1.8 |

Although regeneration was not yet required, the catalyst was regenerated at 44 hours before further use.

TABLE C

| Temp. ° C | 460 | 460 | 475 |
|---|---|---|---|
| Reaction Hours | 2 | 20 | 91 |
| Cumulative Hours Total | 131 | 149 | 220 |
| Product Composition (dry basis) weight % | | | |
| phenol | 30.8 | 30.5 | 32.4 |
| o-cresol | 25.1 | 26.0 | 22.4 |
| m,p-cresol | 7.6 | 5.6 | 4.9 |
| 2,6-xylenol | 25.3 | 31.2 | 36.8 |
| 2,4/2,5-xylenol | 6.6 | 4.4 | 2.3 |
| 2,3/3,5-xylenol | 0.1 | 0.2 | 0.1 |
| 2,4,6-trimethylphenol | 4.3 | 2.1 | 0.9 |

Various catalysts of the instant invention were tested for deactivation times at temperatures of 450°–500° C. Criteria for regeneration was based on o-cresol at 20 weight percent or more (dry basis) of product. The following deactivation times were observed.

| MgO | 50 hours |
|---|---|
| ZnO | 24 hours |
| $WO_3/MgO$ | 140 hours |

EXAMPLE 7

Three weight percent $WO_3$ was added to $SiO_2$ for use as a catalyst. $SiO_2$ (sand) is not a catalyst with respect to the reactions of the instant invention, thus only the catalytic effect of $WO_3$ was tested.

At 460° C and 0.33 LHSV there was negligible reaction of a feed consisting of 60 parts 2,6-xylenol, 40 parts phenol, and 10 parts water. Thus while $WO_3$ is a promoter for MgO catalysts, it is inactive in the absence of MgO.

EXAMPLE 8

A mixture of phenol (50 w/o) and various phenolic compounds were passed over MgO catalyst at 520° C and LHSV 2.0. The feed was a mixture of xylenols having the following composition:

| 2,6-xylenol | 6.0% |
|---|---|
| 2,4-xylenol | 26.2% |
| 2,5-xylenol | 23.6% |
| 2,3-xylenol | 20.8% |
| 2,4,6-TMP | 17.1% |
| 2,3,6-TMP | 4.0% |
| Pentamethyl benzene | 2.0% |
| Other TMP isomers | 0.3% |

In the absence of water at 520° C the product contained 4.6% cresol and 5.3% m,p-cresol. Addition of 3.2% $H_2O$ increased the yield of o-cresol to 12.0% and m,p-cresol yield to 13.2%. A water content of 2–10 w/o has been used.

EXAMPLE 9

A feed consisting of 50 percent 2,3-xylenol, 40.9 percent phenol, and 9.1 percent $H_2O$ (dry basis; 55 percent 2,3-xylenol, 45 percent phenol) was passed over 3 weight percent $WO_3/MgO$ catalyst at LHSV of 0.5 and a temperature of 480° C. The reactor had an internal volume of 180 cc (60 catalyst, 120 inert ceramic saddles). The following product distribution was obtained:

TABLE D

| Temp. ° C | 460 | 460 | 460 | 460 | 460 | 460 | 465 | 480 | 490 | 490 |
|---|---|---|---|---|---|---|---|---|---|---|
| Reaction Hours | 0.5 | 1.5 | 3.75 | 7.25 | 7.25–24 | 29 | 48 | 72 | 120 | 144 |
| Cumulative Hours Total | 220.5 | 221.5 | 223.75 | 227.25 | 227.25–244 | 249 | 268 | 292 | 340 | 364 |
| Product Composition (dry basis) weight % | | | | | | | | | | |
| phenol | 40.1 | 38.4 | 36.2 | 34.1 | 33.6 | 34.2 | 34.2 | 34.4 | 34.4 | 35.4 |
| o-cresol | 7.3 | 12.5 | 16.6 | 20.9 | 22.8 | 21.4 | 21.3 | 20.7 | 21.4 | 18.4 |
| m,p-cresol | 4.3 | 5.1 | 5.7 | 6.3 | 5.8 | 5.2 | 4.8 | 4.3 | 4.7 | 4.1 |
| 2,6-xylenol | 45.7 | 39.6 | 35.5 | 30.9 | 30.3 | 33.3 | 34.7 | 36.5 | 35.3 | 37.6 |
| 2,4/2,5-xylenol | 0.6 | 1.6 | 2.8 | 4.7 | 4.6 | 3.6 | 3.0 | 2.4 | 2.6 | 1.5 |
| 2,3/3,5-xylenol | 0.1 | 0.1 | 0.1 | 0.0 | 0.0 | 0.1 | 0.1 | 0.1 | 0.1 | |
| 2,4,6-trimethylphenol | 1.9 | 2.8 | 3.0 | 3.1 | 2.8 | 2.2 | 1.9 | 1.7 | 1.5 | 1.9 |

| | |
|---|---|
| phenol | 39.5 |
| o-cresol | 4.5 |
| m-cresol | 12.3 |
| p-cresol | 2.7 |
| 2,3-xylenol | 35.0 |
| 2,5-xylenol | 1.4 |
| 2,4-xylenol | 0.5 |
| higher b.p. | 3.7 |

Thus a 2,3-xylenol feed clearly results in a predominantly meta-cresol, ortho-cresol product.

It will be apparent when applying the process of the present invention to that described in the prior art that a simple, effective process for the selective production of meta and para-cresols, increased ortho-cresol production, and a use for xylenol fractions in by-product streams has been provided. The catalysts of the instant invention provide excellent yields and conversion rates.

While certain embodiments and details have been shown for the purpose of illustrating this invention, it will be apparent to those skilled in this art that various changes and modifications may be made herein without departing from the spirit or the scope of the invention.

I claim:

1. An improved process for the conversion of xylenols to cresols by contacting said xylenols with phenol in the presence of magnesium oxide catalysts, the improvement comprising promoting the catalytic activity and catalyst life of magnesium oxide by adding a promotor selected from the group consisting of tungsten oxide or uranium oxide while carrying out the reaction in the vapor phase at temperatures of from about 350° to about 550° C and pressures up to about 1,000 pounds per square inch gauge.

2. A process as described in claim 1 wherein the promoter is tungsten oxide.

3. A process as described in claim 2 wherein the reaction is carried out in a continuous flow reactor.

4. A process described in claim 2 wherein the reaction has an LHSV of from about 0.1 to about 5.0.

5. A process as described in claim 2 wherein the xylenol feed contains from about 1 to about 15 weight percent water.

6. A process as described in claim 2 wherein the xylenols are selected from the group consisting of 2,4-xylenol, 2,5-xylenol, 2,3-xylenol, and 2,6-xylenol and mixtures of these.

7. A process as described in claim 2 wherein the amount of promoter catalyst in the magnesium oxide catalyst is from about .5 to about 15 weight percent of total catalyst weight.

8. A process as described in claim 1 wherein the promoter is tungsten oxide and the activity of the catalyst is further increased by heating the catalyst prior to use in the reaction to about 500° C until no exotherm occurs.

* * * * *